(12) United States Patent
Middlesworth et al.

(10) Patent No.: US 7,507,680 B2
(45) Date of Patent: *Mar. 24, 2009

(54) COMPOSITE ELASTIC WEB

(75) Inventors: Jeffrey Alan Middlesworth, Wauconda, IL (US); Tze Wan Pansy Chung, Fox River Grove, IL (US); Stephen D. Bruce, Crystal Lake, IL (US); James D. Tribble, Brazil, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 193 days.

This patent is subject to a terminal disclaimer.

(21) Appl. No.: 10/705,248

(22) Filed: Nov. 12, 2003

(65) Prior Publication Data

US 2005/0101216 A1    May 12, 2005

(51) Int. Cl.
*D04H 13/00* (2006.01)
*B32B 27/12* (2006.01)

(52) U.S. Cl. .................. 442/328; 442/329; 442/394; 428/131; 428/137; 428/138

(58) Field of Classification Search .............. 442/328, 442/329, 394; 428/131, 137, 138
See application file for complete search history.

(56) References Cited

U.S. PATENT DOCUMENTS

| | | | |
|---|---|---|---|
| 1,981,338 A | 11/1934 | Swift, Jr. | |
| 3,058,868 A | 10/1962 | Schroeder | |
| 3,622,422 A | 11/1971 | Newman | |
| 3,695,967 A | 10/1972 | Ross | |
| 3,854,861 A | 12/1974 | Worrall | |
| 4,379,192 A | 4/1983 | Wahlquist et al. | |
| 4,414,970 A | 11/1983 | Berry | |
| 4,522,203 A | 6/1985 | Mays | |
| 4,573,991 A | 3/1986 | Pieniak et al. | |
| 4,606,338 A * | 8/1986 | Greenway et al. | ............. 602/45 |
| 4,606,964 A | 8/1986 | Wideman | |
| 4,692,368 A | 9/1987 | Taylor et al. | |

(Continued)

FOREIGN PATENT DOCUMENTS

WO   WO 00/59431   10/2000

(Continued)

OTHER PUBLICATIONS

European Search Report for Application No. EP 04 10 5210 dated Sep. 17, 2008, issued by the European Patent Office (2 pages).

*Primary Examiner*—Ula C Ruddock
(74) *Attorney, Agent, or Firm*—Tessari & Associates, pllc; Joseph A. Tessari

(57) ABSTRACT

A method for manufacturing composite webs and composite webs made thereby in which the web includes a perforated thermoplastic film and one or more nonwoven webs. The method provides a perforated thermoplastic film, a creped nonwoven web, the webs are fed in a face to face relationship to be bonded. The perforated thermoplastic film and the creped nonwoven web are bonded in a face to face relationship at a plurality of points of contact such that the creped structure of the nonwoven web is maintained and the composite web has a nonwoven face and a film face. The composite webs are extensible at least in the direction of the creping.

6 Claims, 10 Drawing Sheets

U.S. PATENT DOCUMENTS

| | | | |
|---|---|---|---|
| 4,753,840 A | 6/1988 | Van Gompel | |
| 4,842,596 A | 6/1989 | Kielpikowski et al. | |
| 4,995,930 A | 2/1991 | Merz et al. | |
| 5,035,941 A | 7/1991 | Blackburn | |
| 5,143,679 A | 9/1992 | Weber et al. | |
| 5,382,461 A | 1/1995 | Wu | |
| 5,422,172 A | 6/1995 | Wu | |
| 5,589,014 A | 12/1996 | Hicks | |
| 5,681,302 A | 10/1997 | Melbye et al. | |
| 5,733,628 A | 3/1998 | Pelkie | |
| 5,769,993 A | 6/1998 | Baldauf | |
| 5,861,074 A | 1/1999 | Wu | |
| 6,106,925 A * | 8/2000 | Palumbo | 428/137 |
| 6,114,595 A | 9/2000 | Moore et al. | |
| 6,270,875 B1 * | 8/2001 | Nissing | 428/138 |
| 6,303,208 B1 | 10/2001 | Pelkie | |
| 6,534,694 B2 | 3/2003 | Kling et al. | |
| 6,562,170 B2 | 5/2003 | Thomas | |
| 6,592,697 B2 | 7/2003 | Pike et al. | |
| 2004/0102125 A1 * | 5/2004 | Morman et al. | 442/394 |

FOREIGN PATENT DOCUMENTS

WO  WO 03/017904 A1  3/2003

* cited by examiner

COMPOSITE ELASTIC WEB

FIELD OF THE INVENTION

Embodiments of the present invention relate to elastic laminates including films and fibrous materials that are useful, for example, in diapers, articles to control the effects of incontinence, and other hygiene articles and bandages.

DESCRIPTION OF RELATED ART

Absorbent articles such as diapers, training pants or incontinence garments are required to provide a close, comfortable fit about the wearer and contain body exudates while maintaining skin health. Skin health is believed to be promoted by maintaining a low humidity of the air that is in contact with the skin. In an attempt to reduce the humidity level within such absorbent articles, breathable polymer films that are capable of passing water vapor have been employed as outer covers for such absorbent articles. The breathable films typically are constructed with pores to provide desired levels of liquid impermeability including air and vapor permeability. Other absorbent article designs have been arranged to provide breathable regions in the form of breathable panels or perforated regions in otherwise vapor-impermeable outer covers to help ventilate the articles.

Elastic materials that are intended for use in diapers and other disposable articles to assure a comfortable fit can be made breathable by forming them with holes (e.g., apertures) or three dimensional cones that can pass air. For example, U.S. Pat. Nos. 6,303,208 and 5,733,628 to Pelkie et al., the disclosures of which are incorporated herein by reference in their entirety, disclose permeable vacuum formed three dimensional elastic webs.

In addition to skin health considerations, it is desirable that elastic materials for use in absorbent articles be soft to the touch. Softness can be achieved by laminating the elastic material to a soft and generally fibrous material, such as a nonwoven. Several patents disclose lamination of nonwoven materials and films. For example, U.S. Pat. Nos. 3,058,868 and 4,692,368 disclose stretching extruded polymeric films prior to laminating with unstretched nonwoven fibrous webs at pressure roller nips. U.S. Pat. Nos. 4,522,203 and 5,035,941 disclose co-extruding multiple polymeric films with unstretched nonwoven webs at pressure roller nips. U.S. Pat. No. 4,753,840 discloses pre-forming nonwoven polymeric fiber materials prior to extrusion laminating with films to improve bonding between the nonwoven fibers and films. The '840 patent discloses conventional embossing techniques to form densified and undensified areas in nonwoven base plies prior to extrusion lamination to improve bonding between nonwoven fibrous webs and films by means of the densified fiber areas.

U.S. Pat. No. 5,035,941 discloses using multiple co-extruded film piles to prevent pinhole problems. Methods for bonding loose nonwoven fibers to polymeric film are disclosed in U.S. Pat. Nos. 3,622,422, 4,379,192, 4,379,197 and 6,562,170. U.S. Pat. No. 3,695,967 discloses a method for manufacturing an air-permeable laminate in which nonwovens are laminated to a thermoplastic film by the application of pressure and heat at spaced-apart bonding sites where the film is melted to form apertures.

U.S. Pat. No. 4,414,970 discloses a moisture vapor-transmitting elastic bandage comprising inner and outer layers of fabric bonded to a central layer. The central layer comprises an apertured elastomeric film. The apertured elastomeric film may take the form of a perforated film or a net in which the strands and junctures are formed integrally during manufacture. The fabric layers can be compressed in one direction by bonding to the elastic layer while it is already stretched in one direction. The compression makes the fabric layers extensible.

U.S. Pat. No. 4,995,930, the disclosure of which is incorporated herein by reference in its entirety, describes a process of vacuum lamination of a nonwoven onto a film as it is being formed from the molten state over a vacuum drum. The advantages of vacuum lamination lie in the gentleness with which the nonwoven is treated, so that its bulky properties are not affected by the lamination process. The process also is said to be economical.

A tri-laminate structure often is used in commercial manifestations of laminates for absorbent articles, where the laminate has its outer two layers bonded through the middle, elastic, permeable layer. The tri-laminate has the advantage of having soft and bulky surfaces on both sides of the elastic.

Bonding of the outer layers through the perforations in the elastic layer is a common way of securing the layers together. For example, U.S. Pat. No. 6,534,694, discloses a laminate that comprises a perforated elastic web and two material layers, one on either side of the elastic web, said outer layers being bonded through the perforations. Similarly, U.S. Pat. No. 4,573,991, discloses a three layer structure in which the two outer layers are secured through at least some of the apertures in the center layer. A method for bonding a three layer web is presented in U.S. Pat. No. 5,769,993 in which the two outer layers are welded through the center layer.

U.S. Pat. No. 4,842,596, discloses an elastomeric trilaminate that can be used as the outer cover or as leg and waist gathers in a disposable absorbent garment. The tri-laminate includes a liquid impervious elastomeric film carrier sheet sandwiched and bonded at spaced apart sites between a pair of nonwoven facing sheets. The sheets can be laminated by ultrasonic or thermal bonding. Breathable apertures are formed which laminate the carrier and facing sheets together.

The pleasant feel of a laminated material can be enhanced if the nonwoven is bulked, for example by creping. An example of this technology is disclosed in U.S. Pat. No. 6,114,595, the disclosure of which is incorporated by reference herein in its entirety. This patent discloses creping the non woven and the elastic layer together after lamination so that the overall structure, including the elastic material, has a creped appearance.

An advantage of creping or "crinkling" is described in U.S. Pat. No. 5,681,302 whereby a crinkled web is fed to a station where strands of elastomeric material are extruded onto it. The material formed is disclosed as useful for disposable articles such as diapers.

U.S. Pat. No. 4,606,964 discloses a laminate material that is made while the elastic material is held under differential tensioning forces. The effect on the product structure is said to produce a laminate that is more bulked in some areas than others.

U.S. Pat. Nos. 5,861,074, 5,422,172, and 5,382,461, discloses achieving bulk by stretching the laminate and thereby exposing fibers through the surface of the web, providing a bulked feeling to the web.

All documents described herein are incoporated by reference in their entirety. In addition, the description herein of disadvantages or deleterious results achieved with known products, processes, and apparatus is not intended to limit the invention. Indeed, certain embodiments of the invention may include known products, processes, and apparatus without suffering from the known disadvantages or deleterious results.

SUMMARY OF THE INVENTION

Despite attempts to develop materials for improved absorbent articles, there remains a need for materials that can economically provide elasticity, breathability and softness, while remaining tough enough to withstand the stresses of their intended use. In particular, in laminates that are to undergo activation, there is a need for structures that utilize less expensive, lower basis weight nonwovens without damage during the activation process.

The present invention provides such a material, and a process for manufacturing such a material. The process for manufacturing described herein allows for the formation of a laminated web that comprises an elastic film and a creped nonwoven, and that retains the soft and lofty properties of the original creped nonwoven of which it is comprised. In its preferred embodiment, the process of an embodiment of the invention does not require the expense of using adhesives to bind the nonwoven web and the elastic material.

Creping or puckering of the nonwoven web also is believed to provide an advantage to the product in that it renders the laminate elastic, as the puckered nonwoven is extensible in the direction of puckering. In the absence of such puckering, in order to make the nonwoven and hence the entire laminate elastic, it has to be "activated"-a process that stretches it in one or more directions and modifies the micro and macro structure of the nonwoven web so that it can be elongated in at least one direction. Activation of a nonwoven is disclosed in U.S. Pat. No. 5,143,679, the disclosure of which is incorporated herein by reference in its entirety. The composite webs of the invention offer further advantages by permitting high extension associated with deep engagement during the stretching or "activation" producess, and also permits cold drawing capabilities without tearing the composite or nonwoven layers.

An embodiment of the present invention includes soft and elastic composite materials and to methods of their manufacture. The composite comprises a first layer of non elastic cloth like material, and a porous elastic layer bonded to the cloth like material in a face to face relationship. The first non elastic cloth like material is creped in such a way that it is bonded to the porous elastic layer at discrete points on its surface such that there is enough free unbonded cloth like material that the creped layer can be extended by a tensile force which is applied to the composite to at least 125% of its original length.

Optionally, a second non elastic cloth like material can be bonded to the surface of the elastic layer that is not bonded to the first non elastic cloth like material. The second non elastic cloth like material can be creped or non-creped.

An additional embodiment of the invention is directed towards a process for making a composite that comprises a first layer of non elastic cloth like material, and a porous elastic layer bonded to the cloth like material in a face to face relationship. The process involves creping the first non elastic cloth like material in a creping process, and delivering as a web to a bonding station in which the first non elastic cloth like material is bonded to a perforated thermoplastic web in such a way that there is enough free unbonded cloth like material that the creped layer can be extended by a tensile force that is applied to the composite to at least 125% of its original length.

In a preferred embodiment of the invention, the creping, perforating and bonding processes all occur at the same station, with the perforating and bonding steps occuring essentially simultaneously.

A process of an embodiment of the invention also allows for the manufacture of a laminate web that is suitable for subsequent activation and that comprises a nonwoven web that is less bulky and of lower basis weight than heretofore possible for the process of activation.

BRIEF DESCRIPTION OF THE DRAWINGS

The features and advantages of the invention will be better understood with reference to the following description, claims and drawings, where:

DETAILED DESCRIPTION OF THE PREFERRED EMBODIMENTS

Figure 1:
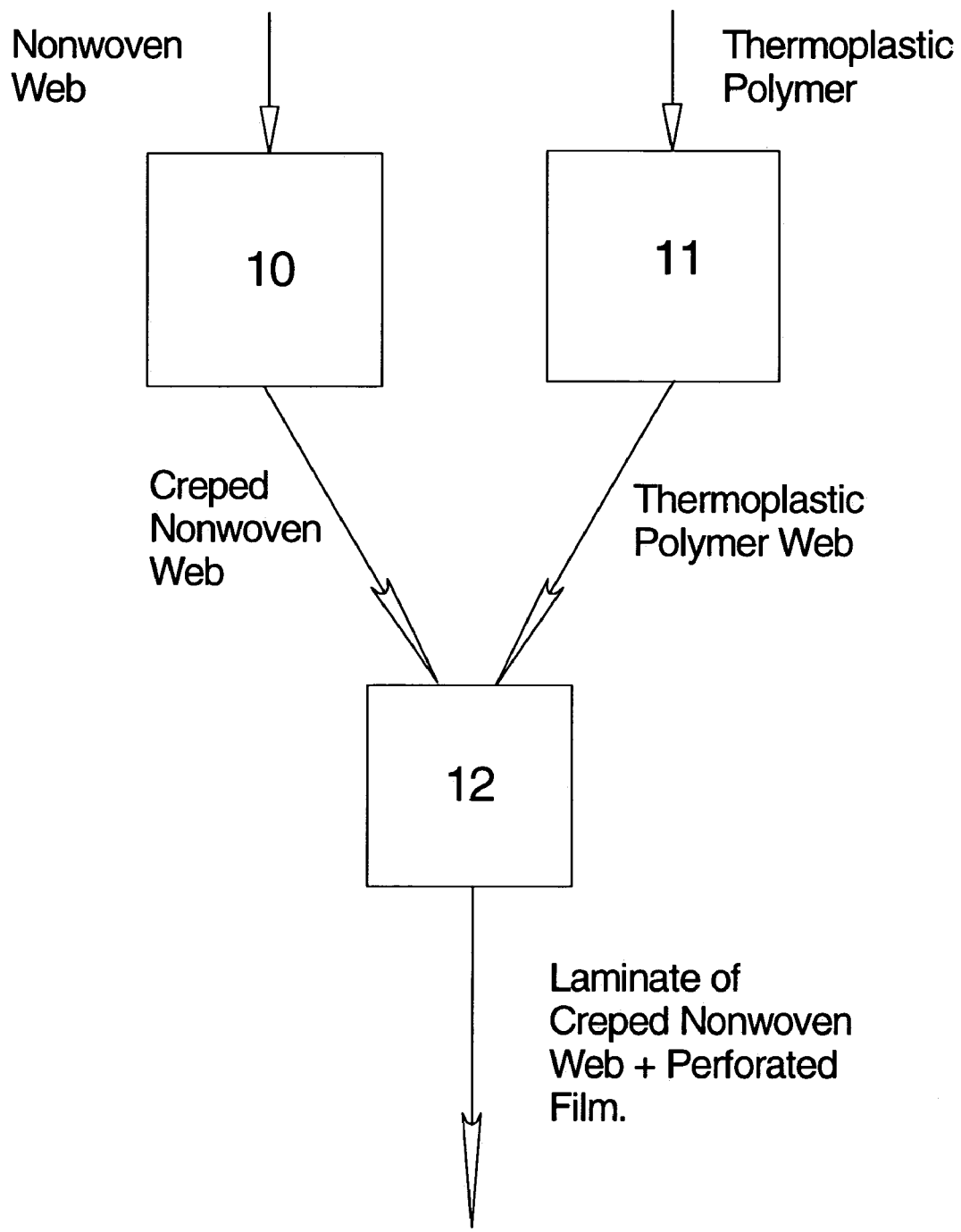
FIG. 1 is a process flow chart that describes the process involved in a preferred method of the present invention and in manufacturing a preferred composite of the invention.

Throughout this description, the term "substantially" means that a given property or parameter (such as the surface angle) may vary by about 30% from the stated value.

The term "permeability" refers to the permeability of vapor or liquid.

The term "web" refers to a material capable of being wound into a roll. Webs can be film webs, nonwoven webs, laminate webs, apertured laminate webs etc.

The term "film" refers to a web made by extruding a molten sheet of thermoplastic polymeric material by a cast or blown extrusion process and then cooling the sheet to form a solid polymeric web. Films can be monolayer films, coextruded films, coated films, and composite films. Coated films are films comprising a monolayer or coextruded film which are subsequently coated (for example, extrusion coated, impression coated, or printed) with a thin layer of the same or different material to which it is bonded and after bonding is incapable of separation. Composite films are films comprising more than one film where at least two films are combined in a bonding process. Bonding processes may incorporate adhesive layers between the film layers. Films also denote cast films that are not made using an extrusion process.

Throughout this description, the expression "apertured film" denotes a film having a plurality of holes that extend from one surface to a second surface. A two dimensional apertured film is a film in which no three dimensional structure exists in or around the holes, which then connect the second surface of a flat film to the first surface of the film. A three dimensional film is a film with protuberances or other dimensional structures.

The term "nonwoven" means a web including a multitude of fibers. The fibers can be bonded to each other or can be unbonded. The fibers can be staple fibers or continuous fibers. The fibers can comprise a single material or a multitude of materials, either as a combination of different fibers or as a combination of similar fibers each comprised of different materials.

A nonwoven fibrous web useful in embodiments of the invention may comprise fibers of polyethylene, polypropylene, elastomers, polyesters, rayon, cellulose, nylon, and blends of such fibers. A number of definitions have been proposed for nonwoven fibrous webs. The fibers usually include staple fibers or continuous filaments. As used herein "nonwoven fibrous web" is used in its generic sense to define a generally planar structure that is relatively flat, flexible and porous, and is composed of staple fibers or continuous filaments. For a detailed description of nonwovens, see "Nonwoven Fabric Primer and Reference Sampler" by E. A. Vaughn, ASSOCIATION OF THE NONWOVEN FABRICS INDUSTRY, 3d Edition (1992). The nonwovens may be carded, spun bonded, wet laid, air laid and melt blown as such products are well known in the trade.

The nonwoven web of the present invention can be the product of any process for forming the same. Examples of methods for manufacturing non woven webs that are well known to those skilled in the art are the processes that produce spunbond and melt blown non woven webs. The non woven web of which embodiments of this invention comprise can also be a composite or combination of webs, such as spunbond or melt blown webs. In a preferred embodiment of the invention, the web is a spunbond material made of polypropylene fiber. However, the non woven web can comprise any polymeric material from which a fiber can be produced.

Throughout this description, "extensibility" of a web refers to the amount of strain (in %, relative to the zero strain state) that can be applied to a web by a tensile force without breakage of fibers, bonds between fibers or undue distortion of the web structure. For a nonwoven web to be extensible in any given direction means that when a tensile force is applied to the web in that direction, the web expands in that direction, and a strain is induced in the web, substantially without breakage of fibers, or of bonds between fibers. The extensibility of a creped web has two components. One is the "instrinsic extensibility" of the web, that referes to the extensibility of the web in its natural, uncreped, state. The second component is the "crepe induced extensibility", which refers to the strain that can be applied to extend the web in a given direction by virtue of the creping structure. It can be seen, for example, that after a creped web has been stretched to the point of "crepe induced extensibility," the web is essentially in its uncreped state.

The term "composite web" denotes a web comprising at least two Webs bonded to each other in a face to face relationship.

The term "perforation" as used herein refers to an aperture in the screen. The term "screen" as used herein refers to a three-dimensional molding apparatus comprising indentations used to form protuberances or apertures in films. In a particularly preferred embodiment screens comprise tubular members, having a width and a diameter. In alternative embodiments, screens comprise belts having a width and a length. The transverse direction is the direction parallel to the width of the screen. The machine direction is the direction parallel to the direction of rotation of the screen, and is perpendicular to the transverse direction.

The term "protuberance" as used herein refers to a three-dimensional member comprising an apertured base portion located in the plane of the first surface of the film and a sidewall portion extending generally in the direction of the second surface of the film. Each base portion has a sidewall portion. Sidewall portions terminate in "ends" located in the plane of the second surface of the film. The ends of the protuberances may be apertured or unapertured. The apertures in the base portions of the protuberances, also called "primary apertures", are preferably in the shape of polygons, e.g., squares, hexagons, pentagons, ellipses, circles, ovals, slots, etc., in a regulated or random pattern. The protubered ends, if apertured, are called "secondary apertures", and are preferably in the shape of polygons, e.g., squares, hexagons, pentagons, ellipses, circles, ovals, slots, etc.

As used herein, the term "absorbent article" denotes articles that absorb and contain fluids and other exudates. More preferably, an absorbent article includes garments that are placed against or in proximity to the body of a wearer to absorb and contain the various exudates discharged from a body. A non-exhaustive list of examples includes absorbent towels, diapers, training pants, absorbent underpants, adult incontinence products, and feminine hygiene products.

The terms "creped" and "puckered" are synonymous as used herein and are used to describe a web material having arcuate structures extending from one surface that are continuous with the surface of the material. A corrugated structure would be an example of such a puckered structure. A creped structure as defined for the purposes of this disclosure also includes a structure in which the arcuate structures do not extend from one edge of the web material to the other. The structures can therefore have the appearance of "molehills" when viewed under a magnifying lens. No limitation on the size of the arcuate structures is implied by the use of the terms "creped" or "puckered".

Various methods for producing a creped web are described in several patents. Nearly every embodiment of creping technology has in common the feature that a web is forced into a shape with arcuate structures. Then, the creped material typically is stabilized to ensure that it maintains its creped structure when the creping force is removed. If the structure has been especially softened before creping, then it usually is stabilized by reversing the softening process. For example, if it has been wetted, then it is dried, or if it has been thermally softened, then it is cooled. As used herein, the term "stabilized" refers to a creped web that is able to retain its structure in the absence of a creping force.

If the structure has not undergone a permanent deformation, then it can be bonded to, for example a backing sheet through the application of adhesive to the top of the arcuate structures and nipping with the backing sheet.

For example U.S. Pat. No. 1,981,338, incorporated herein by reference in its entirety, describes an apparatus for making corrugated paper board in which paper is passed over a toothed wheel to which it is adhered by a vacuum. Adhesive is applied to the tips of the corrugations and the corrugated paper is then released from the toothed wheel and adhered to a backing sheet.

U.S. Pat. No. 3,854,861, incorporated herein by reference in its entirety, also describes an apparatus for producing corrugations. A corrugated roll is hollow, and holds a sheet to be corrugated to it by means of vacuum, and releases it by means of air pressure. In a further example of a process that produces a corrugated web, U.S. Pat. No. 5,589,014, incorporated herein by reference in its entirety, describes a method for producing pleats by means of a vacuum, and then bonding it in order to stabilize it.

Throughout this description, the expression "creping roll" is used to describe a roll over which a web is passed in order to impart a creped structure to it. The roll can be grooved, with teeth running axially around its circumference, or it can be substantially smooth (un-toothed) with an embossed surface. The creping roll also can be perforated and a vacuum can be applied through the perforations from the inside of the roll in order to force the web into substantial conformance to the shape of the roll surface. The creping roll also can be used in conjunction with a second roll that forces the web to be creped onto the surface of the roll. A suitable example includes two geared rolls, in which the teeth of one roll pushes a web into the grooves in a second roll.

The creping roll also can be used in conjunction with a creping knife. U.S. Pat. No. 6,592,697, the disclosure of which is incorporated herein by reference in its entirety, describes a creping process that can be incorporated into the present invention, and a stabilized creped web that can be used as a feedstock for the present invention.

As will be appreciated by those skilled in the art, there are other methods available to the practitioner to produce and also stabilize a creped web for use in the present invention, and the invention is not limited in its mode of operation to those methods described above.

Materials suitable for making the film preferably are mixed and heated in a mixing and heating apparatus. Any mixing and heating apparatus and method can be used in the invention. A particularly preferred mixing and heating apparatus and methods are extrusion apparatus and processes. Extrusion processes are well known in the art, and any suitable extrusion process can be used to prepare the melt sheet of the present invention, using the guidelines provided herein. These extrusion processes usually comprise mechanisms for feeding materials to the extruder, mechanisms for melting and mixing materials, mechanisms for transporting the molten materials to a forming die and mechanisms for cooling the molten sheet of polymer to form a polymer film. In case a second film or web is laminated to the molten sheet, such second film or web may participate in the cooling process.

Methods and apparatus suitable for feeding the raw materials to the extruder generally are known. A preferred feeding mechanism comprises a conveying mechanism such as a vacuum pump connected to a vacuum pipe, the pipe being submerged in a reservoir of polymer material. In a controlled manner the pump generates vacuum in the pipe causing the pipe to suction polymer from the reservoir and to deposit it in a feed hopper. The feed hopper typically contains a metering device that deposits accurately controlled amounts of polymer into the extruder receiving cavity. Multiple cavities and feed hoppers may be present in a single extruder thereby enabling feeding of multiple components. In addition, anti-static and vibratory devices can be positioned at or near the feed hoppers to assist in accurately dosing the polymer. Other feeding mechanisms known to those skilled in the art or later discovered also are contemplated for use in the present invention.

A preferred melt forming die is a cast die, but other types of dies are possible such as blown film dies. The die forms a molten polymer sheet that is subsequently cooled to create a film or a laminate structure. In an alternative arrangement, the molten polymer exits the extruder through a pelletizing die (a flat, cylindrical plate with multiple small openings). As the polymer passes through the die it forms strings of polymer. The strings may be subsequently cooled and cut by a rotating knife and the cut strings typically are called "compounded pellets". Compounded pellets then can be transported to a second extruder where they are melted again, transported to a die, and formed into a sheet that is subsequently cooled to form a film or laminate structure. In yet another alternative arrangement, the compounded pellets are combined with other polymer pellets in the second extruder. In an additional embodiment, the strings of polymer are not cooled but rather conveyed (as strings through a die, or as a melt plug through the extruder via a screw or the like) through the extruder to the die that forms the melt into a sheet.

Cooling mechanisms also are well known in the art and any cooling mechanism now known or later discovered can be used in the present invention. A primary cooling mechanism can include an embossing station comprising two cooled rolls that are pressed against each other. The molten polymer usually is caused to pass between the embossing rolls (called engraving and anvil rolls, respectively) where it is cooled by contact with the cooler rolls. Alternatively, the rolls can both be smooth chill rolls without an engraving or embossing roll. Another well known cooling device comprises passing the polymer sheet over a single roll and applying an air or cool water curtain to the molten polymer to cause it to contact the single cooling roll. Both the air curtain and the contact with the roll contribute to cooling.

Another well known cooling mechanism comprises passing the polymer sheet over an apertured screen while in the presence of vacuum. Vacuum causes the polymer sheet to come into close contact with the screen causing the polymer to cool. In one embodiment, the vacuum and screen combination cause the polymer sheet to conform to the shape of the apertured screen surface to form protrusions in the film. The side of the film that contacts the screen is called the formed film inner surface and the side of the film that is opposite the inner surface is called the formed film outer surface. The protrusions can be apertured, or they can be unapertured. Forming apertured polymer films in this manner is well known in the art.

One of the earlier methods for vacuum perforation of a polymeric film is disclosed in Zimmerli, U.S. Pat. No. 3,054,148, incorporated herein by reference in their entirety. The patentee describes a stationary drum having a screen mounted around the outer surface of the drum and adapted to freely rotate thereon. A plasticized thermoplastic material is applied onto the screen. A vacuum chamber is employed beneath the screen to create a pressure differential between the respective surfaces of the thermoplastic sheet to be perforated to cause the plasticized sheet material to flow into openings provided in the screen and thereby cause a series of openings, holes or perforations to be formed in the plastic sheet. Zimmerli discloses a method for making a film with tapered protuberances. A variety of methods and apparatus including different types of perforating screens have been developed over the years since Zimmerli's invention for making apertured films. Examples of such methods and apparatus are described in U.S. Pat. Nos. 4,155,693, 4,252,516, 4,508,256, and 4,509,908, the disclosures of each of which are incorporated herein by reference in their entirety.

Other means of perforation include passing the film over a perforating roll from which pins or blades project, which enter the film and produce holes as the film passes over the roll. In these methods, a backing roll is generally used that holds the film in place against the perforating roll. The actual perforation then takes place in the nip between the perforating roll and the backing roll.

"Bonding means" in the context of this invention refers to the manner in which lamination of two webs into a composite structure is accomplished. Methods that are suitable in the context of this invention are exemplified by, but not limited to, ultrasonic bonding, point bonding, vacuum lamination, and adhesive lamination. Those skilled in the art are familiar with the various types of bonding, and are capable of adapting any suitable bonding means for use in the invention.

Ultrasonic bonding typically entails a process performed, for example, by passing a material between a sonic horn and an anvil roll such as illustrated in U.S. Pat. Nos. 4,374,888 and 5,591,278. In an exemplary method of ultrasonic bonding, the various layers that are to be attached together are simultaneously fed to the bonding nip of an ultrasonic unit. A variety of these units are available commercially. In general, these units produce high frequency vibration energy that melt thermoplastic components at the bond sites within the layers and join them together. Therefore, the amount of induced energy, speed by which the combined components pass through the nip, gap at the nip, as well as the number of bond sites determine the extent of adhesion between the various layers. Very high frequencies are obtainable, and frequencies in excess of 18,000 cps (cycles per second) are usually referred to as ultrasonic, depending on the desired adhesion between various layers and the choice of material, frequencies as low as 5,000 cps or even lower may produce an acceptable product.

Point bonding typically refers to bonding one or more materials together at a plurality of discrete points. For example, thermal point bonding generally involves passing one or more layers to be bonded between heated rolls, for example, an engraved pattern roll and a smooth calender roll. The engraved roll is patterned in some way so that the entire fabric is not bonded over its entire surface, and the calender roll is usually smooth. As a result, various patterns for engraved rolls have been developed for functional as well as aesthetic reasons.

Adhesive lamination usually refers to any process that uses one or more adhesives that are applied to a web to achieve a bond between two webs.

The adhesive can be applied to the web by means such as coating with a roll, spraying, or application via fibers. Examples of suitable adhesives are given in U.S. Pat. No. 6,491,776, the disclosure of which is incorporated herein by reference in its entirety. In the present invention, the adhesive would be applied to the "high points" of the creped structure of the creped nonwoven web. The nonwoven web and the film then would be brought into contact under conditions of heat and pressure that are suitable for a bond to be formed.

U.S. Pat. Nos. 4,995,930, 5,591,510, 5,635,275, 5,635,276, 5,660,882, 5,698,054, 5,762,643, 5,733,628, 5,783,014, 6,242,074, and 6,303,208 each describe a lamination technique called vacuum formed lamination (VFL), whereby a web substrate is laid upon a molten polymer sheet as successive portions of the sheet are passed over an apertured screen under the presence of vacuum. The disclosures of each of these patents are incorporated herein by reference in their entirety. The web substrate can be a nonwoven or it may be a thin polymeric substrate, breathable or non-breathable. The substrate may be a monolayer or multilayer substrate.

Activation refers to the process of stretching a material beyond the total extensibility of the nonwoven web or webs which it comprises (see the definition of "extensibility," above). The activation generally is accomplished by one of two processes. One is stretching in a set of intermeshing gears, and the other is stretching between driven rolls in the machine direction of the web.

Intermeshing Gear (IMG) machine direction orientation typically is accomplished by stretching the film through a gear-like pair of rollers. The shafts on which the rollers are mounted are positioned between two machine side plates, the first shaft being located in fixed bearings and the second shaft being located in bearings in slidable members. The position of the slidable members is adjustable by means of wedge shaped elements operable by adjusting screws or other devices. Screwing the wedges out or in will move the vertically slidable member respectively down or up to further engage or disengage the gear-like teeth of the second intermeshing roll with the first intermeshing roll. Micrometers mounted to the side frames indicate the depth of engagement of the teeth of the intermeshing roll.

Air cylinders usually are used to hold the slidable members in their engaged position firmly against the adjusting wedges to oppose the opposing force exerted by the material being stretched. These cylinders may also be retracted to disengage the upper and lower intermeshing rolls from each other for purposes of threading material through the intermeshing equipment or in conjunction with a safety circuit which would open all the machine nip points when activated.

A drive mechanism typically is utilized to drive the stationery intermeshing roll. If the second intermeshing roll is to be disengageable for purposes of machine threading or safety, it is preferable to use an antibacklash gearing arrangement between the second and first intermeshing rolls to assure that upon reengagement the teeth of one intermeshing roll always fall between the teeth of the other intermeshing roll, thereby avoiding potentially damaging physical contact between addendums of intermeshing teeth. If the intermeshing rolls are to remain in constant engagement, the second intermeshing roll typically need not be driven. The second intermeshing roll may be driven by the driven intermeshing roll through the material being stretched. The teeth typically are not designed to transmit rotational torque and do not contact metal-to-metal in normal intermeshing stretching operation.

An example of the preferred embodiment for use in creping the web of an embodiment of the invention is the equipment made by Northern Engraving and Machine, of Green Bay, Wis., which employs rollers with a tooth pitch, W=0.155". However, a pitch of about 0.040" to about 0.250" also is acceptable. The tooth depth preferably is about 0.280". However, a tooth depth of about 0.030" to about 0.500" also is acceptable. The tooth density at the roll circumference preferably is about one tooth per degree of angle subtended at the circumference of the roll. A particularly preferred embodiment of the invention employs IMG rollers that can be temperature controlled from about 50° F. to about 21° F., more preferably, within a temperature range of from about 70° F. to about 190° F. Even more preferred temperature ranges for use in the invention range anywhere from about about 85° F. to about 180° F., and the most preferred temperature range is from about 95° F. to about 160° F. The roll temperature may be maintained through the use of an internal flow of a heated or cooled liquid, an electrical system, an external source of cooling/heating, combinations thereof and other temperature control and maintenance methods that will be apparent to those of ordinary skill in the art. The preferred embodiment is internal flow of a heated or cooled liquid through the rollers.

The depth of engagement of the roller teeth determines the degree of elongation that the web is subjected to. A balance usually is drawn between the depth of engagement of the roller teeth and the precursor web composition, as many physical properties of the web are affected. Some of the factors affecting the choice of pitch, teeth depth and depth of engagement include the composition of the web,, desired final properties (breathability, absorbency, strength, cloth-feel) and the width of the IMG rollers. The final application of the web also affects these choices because it determines desired final properties. The width of the IMG rollers presents economic and technical limitations—as the width increases, the weight of the rollers also increases as does the amount of deflection experienced by the rollers. Deflection creates variation not only in the process of stretching, but also in the process of making the rollers, particularly as the pitch and tooth depth increases. Those skilled in the art are capable of determining suitable pitch, teeth depth and depth of engagement for use in the invention, using the guidelines provided herein.

Stretching between driven rolls in the machine direction can be accomplished by running a web over two rolls and running the second roll at a speed that is faster than the speed of the first roll, so that if the coefficient of friction between the web and the rolls is sufficiently high, the web is forced to stretch in the gap between the two rolls.

The film of embodiments of the invention can be comprised of a polymer, such as polyethylene, e.g., low density polyethylene (LDPE), linear low density polyethylene (LLDPE) or a mixture of LDPE and LLDPE, polypropylene and combinations thereof, or other polymers now known or later discovered. In one embodiment, the film is made from a mixture of at least about 10% by weight, or about 10% to about 50% by weight of MDPE and the remainder LDPE, LLDPE or a blend of LDPE and LLDPE. The film may also be made from a mixture of at least 10% by weight, or about 10% to about 50% by weight of HDPE and the remainder LDPE, LLDPE or a blend of LDPE and LLDPE. Each of the material formulations can include additional materials, usually in small percentages relative to the polymer, for example processing aids, colorants (e.g. whiteners) and surfactants. The use of the term LLDPE here also includes those LLDPE's that are made using metallocene catalysts and are commonly referred to as mLLDPE, as well as LLDPE made using conventional catalysts, such as Ziegler-Natta catalysts, and the like.

The film layer of the invention also can be made from any suitable elastic material, such as natural or synthetic polymeric materials. Examples of suitable polymers include low crystallinity polyethylenes, metallocene catalyzed low crystallinity polyethylene, ethylene vinyl acetate copolymers (EVA), polyurethane, polyisoprene, butadiene-styrene copolymers, styrene block copolymers such as styrene/isoprene/styrene (SIS), styrene/butadiene/styrene (SBS), or styrene/ethylene-butadiene/styrene (SEBS) block copolymers. Blends of these polymers alone or with other modifying elastic or non-elastomeric materials are also contemplated being useful with the present invention. In certain preferred embodiments, the elastomeric materials can comprise high performance elastomeric materials such as elastomeric block copolymers. An example of a suitable elastomeric block copolymer is sold under the brand name KRATON®, a registered trademark of the Kraton Polymers U.S. LLC.

Turning now to the figures, FIG. 1 depicts a process flow chart of an example of the process of an embodiment of the present invention. A nonwoven web is fed to a creping device 10, where it is creped and fed to a bonding station 12. The creping process can be any process that produces a web that is creped and stabilized and whose structure is stable enough to be fed over the required distance to the bonding and perforation station. An example of a suitable creping process is provided in U.S. Pat. No. 6,592,697, which is cited above. Those skilled in the art will understand that there are other processes that produce a stable creped web that are suitable for use in this invention. In addition, skilled artisans will appreciate that creping may be executed as a stand alone unit operation or as part of a larger continuous process of film making and bonding.

In the example of FIG. 1, a thermoplastic polymer also may be fed, normally in pellet form, to a forming station 11 for producing a thermoplastic perforated polymer web. An example of a forming station would be an extruder and cast film die, followed by a mechanism for perforating the film. Pellets are preferable for feeding to the forming station, although any suitable form for the thermoplastic polymer may be used in the embodiments of the invention. The product from bonding station 12 is a laminate of a creped web with a perforated thermoplastic polymer web.

Figure 2:
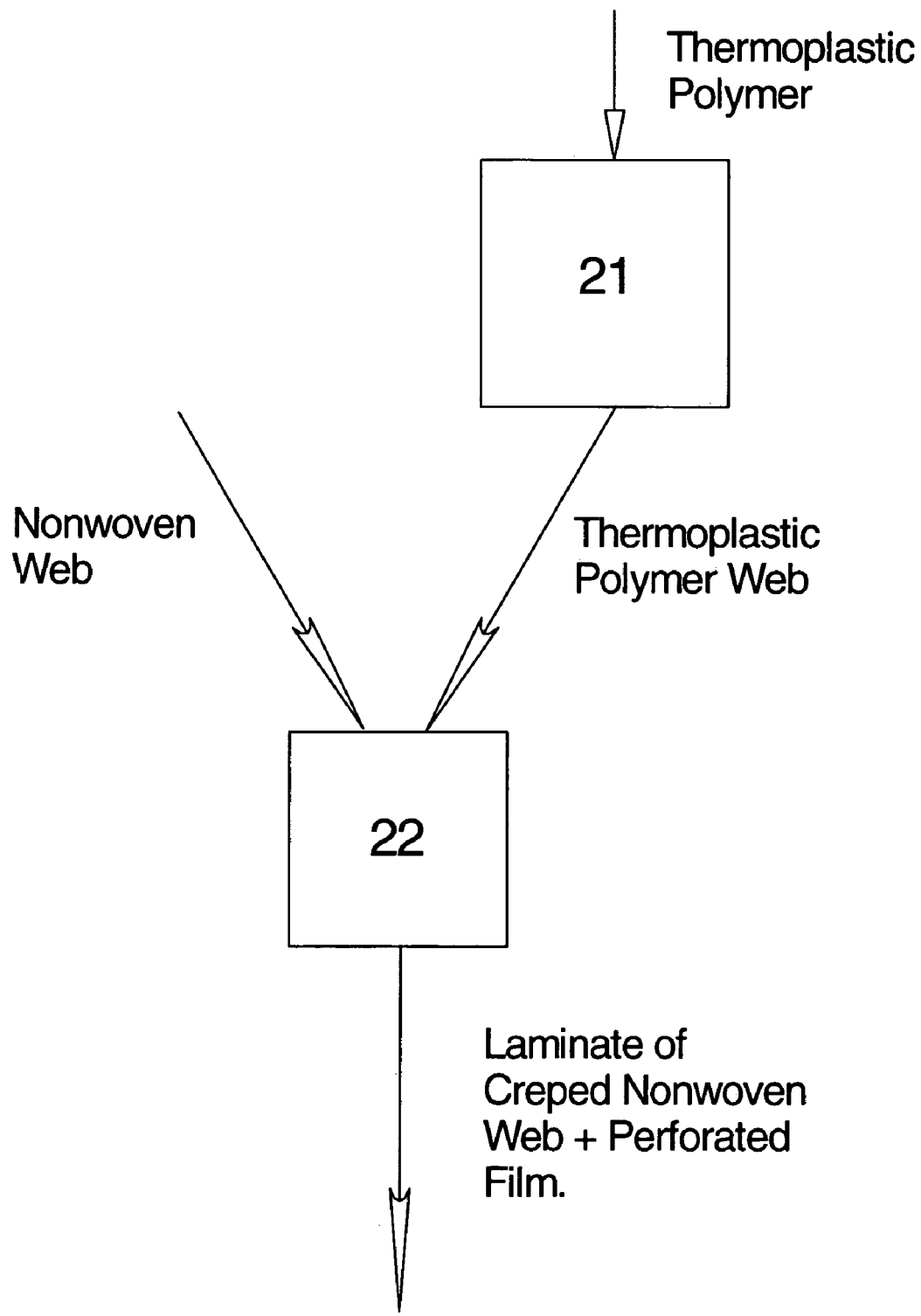
FIG. 2 is a process flow chart that exemplifies the process involved in a preferred embodiment of the method of the present invention.

FIG. 2 illustrates a preferred embodiment of the process of an embodiment of the invention in which a nonwoven web is fed in an uncreped form together with the product of the forming station 21, to a single station 22 in which creping, bonding and perforation all are carried out. In this embodiment, the creping process is carried out on equipment that is integrated with the bonding and perforation equipment, and so, as will be appreciated by one skilled in the art, there is a significant economic and operational advantage in there being no need to stabilize the creped web prior to it being bonded to the perforated web.

Figure 3:
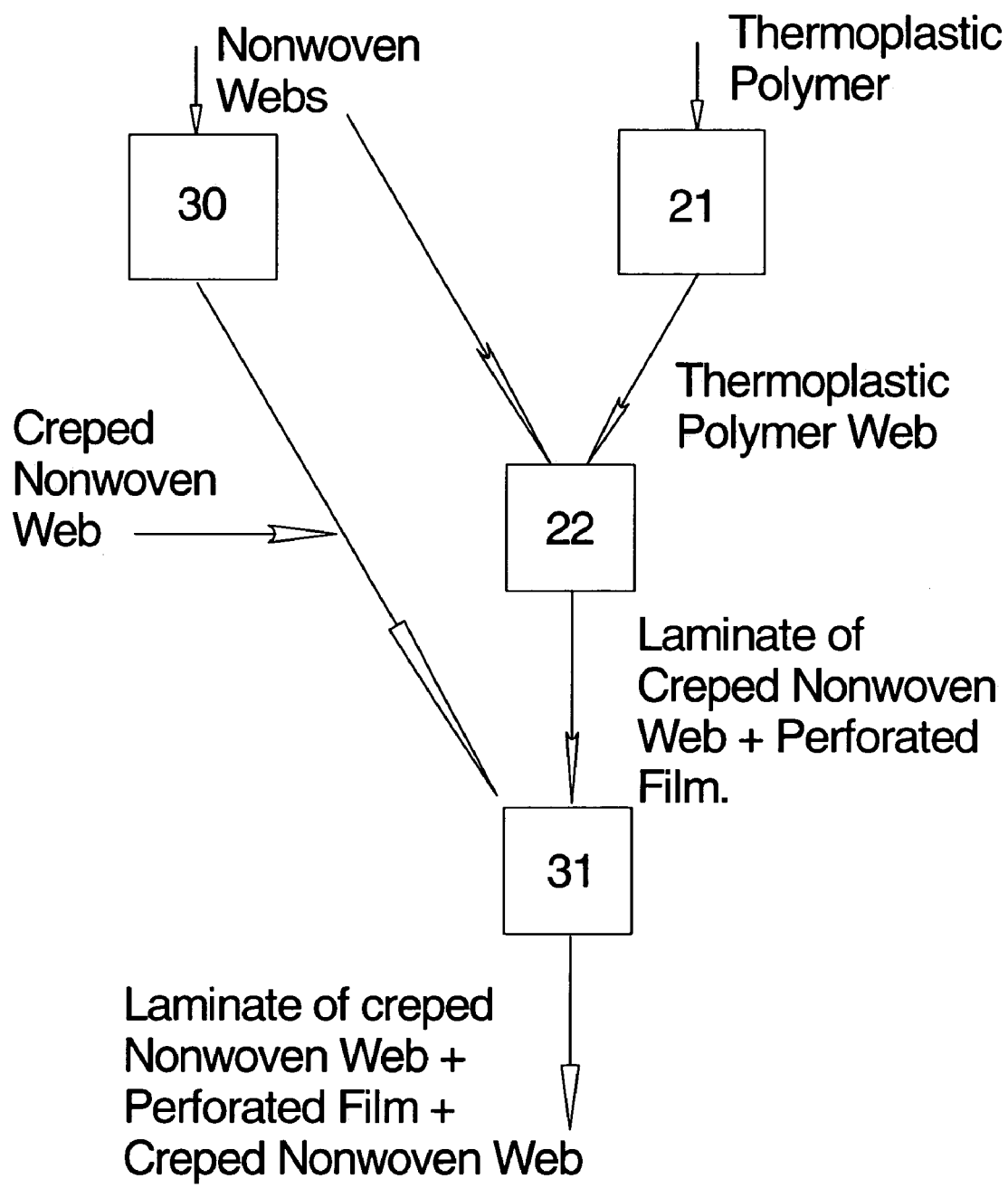
FIG. 3 is a process flow chart of an additional preferred embodiment of the invention in which a second creped nonwoven web is bonded to the composite that is made by the process of FIG. 2.

FIG. 3 illustrates a further extension of a preferred embodiment of an embodiment of the process of the invention in which a second creped web is fed from a creping station 30 into a bonding station together with the product from the bonding and creping station 22. The product of station 30 is thereby laminated onto the film surface of the composite web from station 22 at lamination station 31.

Figure 4:
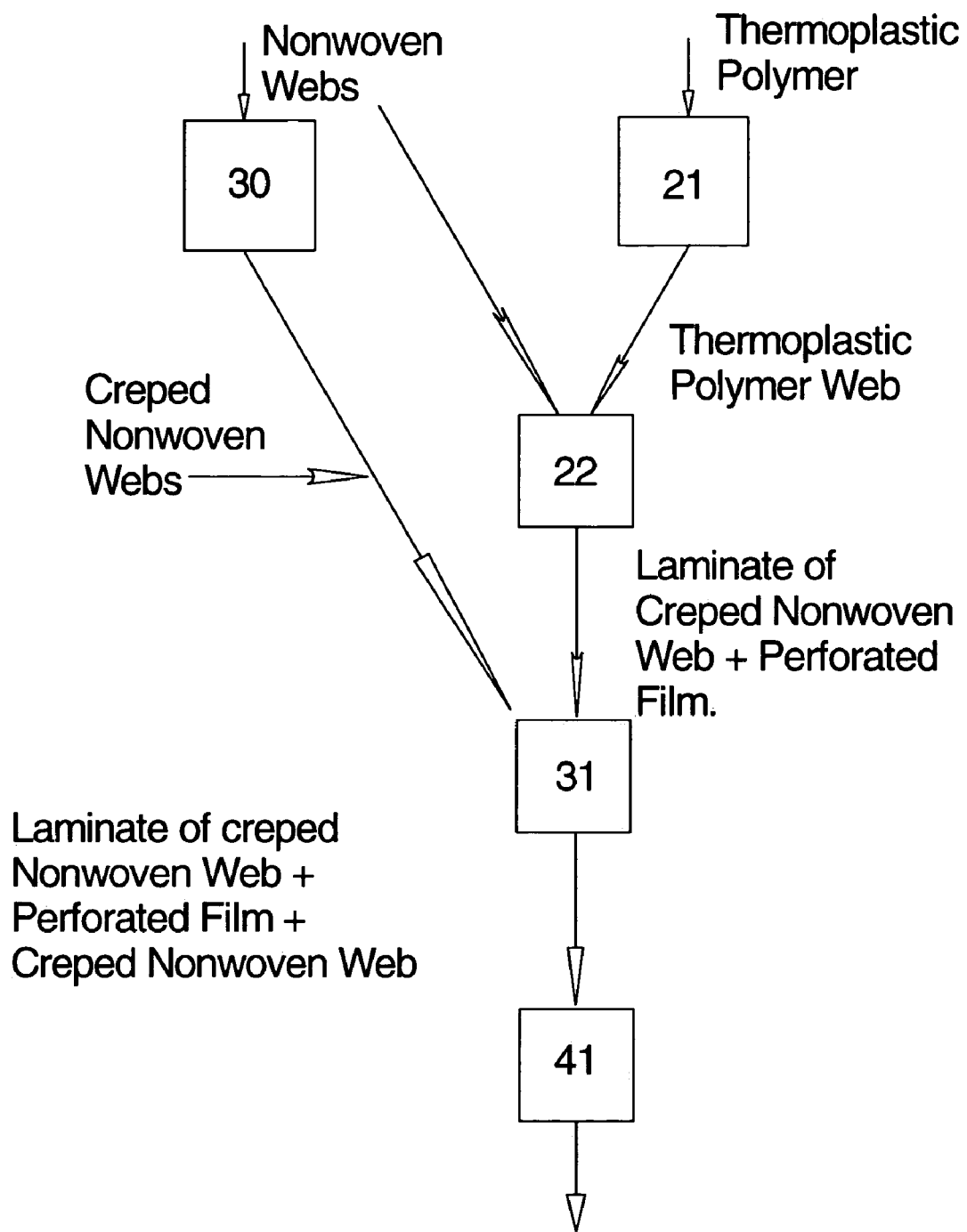
FIG. 4 is a process flow chart of an extension of the process of FIG. 3 in which the composite web that is produced by the process of FIG. 3 is activated.

FIG. 4 illustrates an additional embodiment of a complete process for manufacturing a composite that comprises a creped nonwoven web laminated to a perforated web and then activated by stretching of the composite in the direction of extensibility of the creped nonwoven web. Stretching can be accomplished in stretching station 41 by any of the processes described above.

Figure 5:
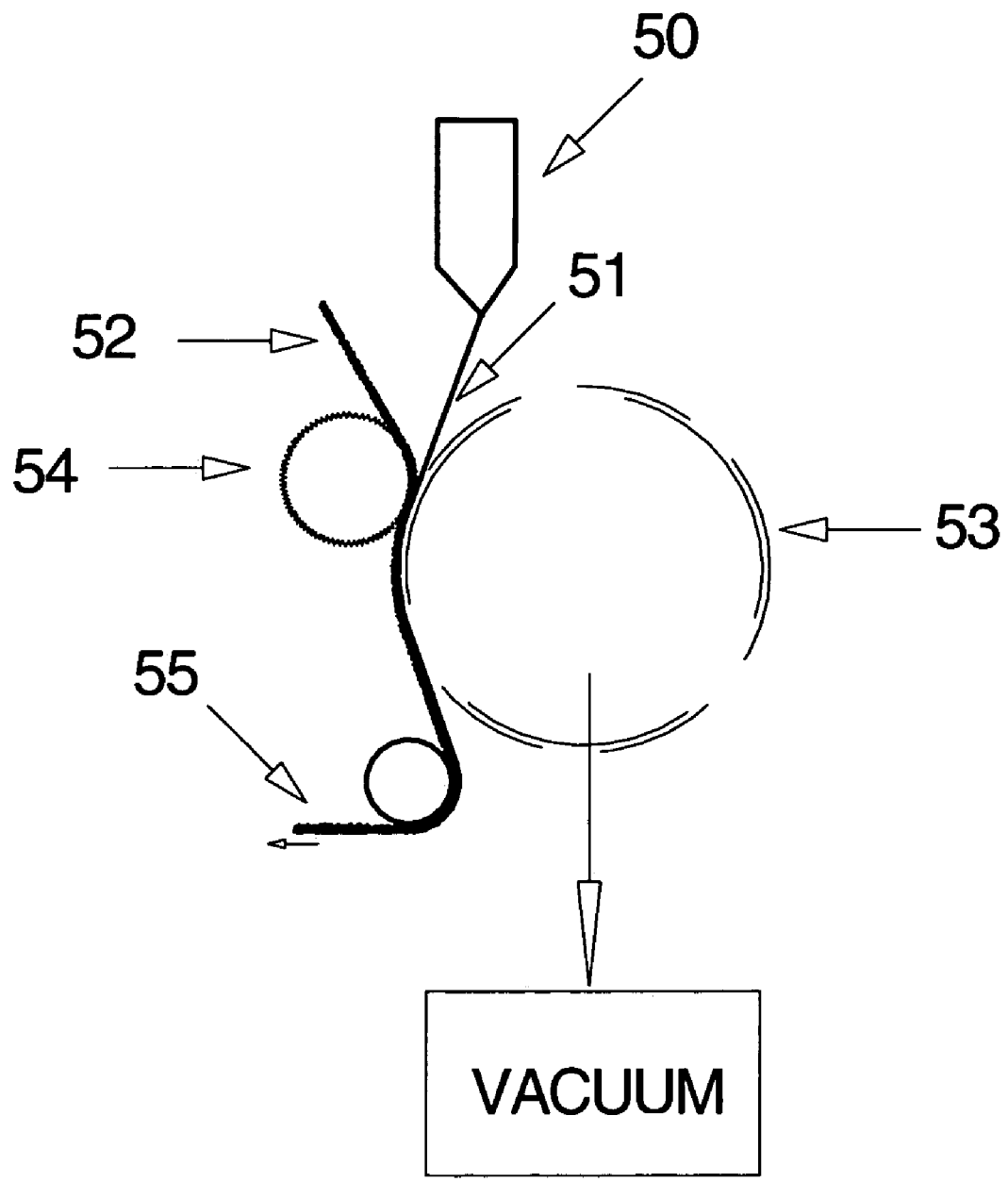
FIG. 5 is a schematic cross section of an example of a preferred manufacturing process of the present invention.

FIG. 5 illustrates a schematic representation of an example of an end view of an apparatus capable of executing an embodiment of the method of the invention. In accordance with this preferred embodiment, a film die 50 is supplied with molten thermoplastic resin and produces a molten sheet 51 of resin in a thermoplastic state. The sheet 51 impinges on a rotating perforated screen 53 from which a vacuum is drawn. The vacuum pulls perforations into the sheet and the motion of the screen draws it into a film.

Simultaneously with the perforation of the sheet, a creped nonwoven web 52 is fed into the nip over a lay on roll 54. The lay on roll 54 can have a surface morphology such that the creped web is able to at least partially conform to the shape of the surface, which minimizes any deleterious impact of the pressure of the roll against the screen. In a preferred embodiment, the lay on roll is a toothed gear roll, which has a tooth density that corresponds to the period of the crepes in the creped web. As a result of the conformity of the creped web with the surface of the lay on roll, the creped web bonds to the film as it is being perforated with substantially no loss of crepe and without either the bonding of the nonwoven web being affected, or the fibers in the nonwoven web being forced to yield. The product 55 is drawn off the screen using a take off roll.

Figure 6:
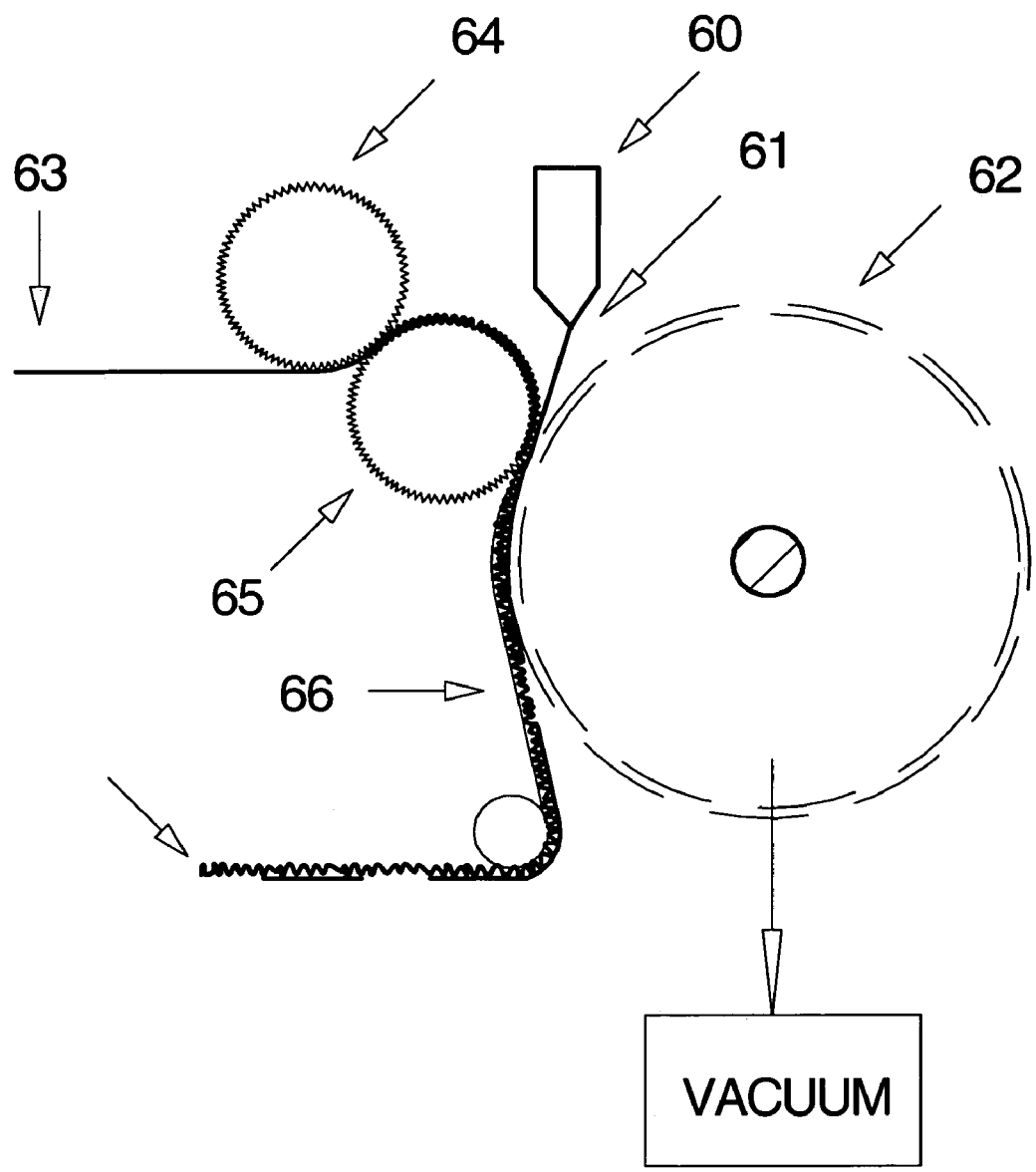
FIG. 6. is a schematic cross section of an example of a preferred manufacturing process of the present invention in which a nonwoven is crepe integrally with the equipment that perforates and laminates the film.

FIG. 6 illustrates a schematic representation of an example of an end view of an apparatus capable of executing another preferred embodiment of the method of the invention. A film die 60 is supplied with molten thermoplastic resin and produces a molten sheet 61 of resin in a thermoplastic state. The sheet 61 impinges on a rotating perforated screen 62 from which a vacuum is drawn. The vacuum pulls perforations into the sheet and the motion of the screen draws it into a film.

Simultaneously with the perforation of the sheet, a nonwoven web 63 is fed into the nip between two rollers (64, 65), preferably toothed (or intermeshing gear) rollers (64, 65). The speed of the web 63 entering the nip usually is addjusted to allow the teeth on roll 64 to have the effect of pushing the nonwoven web into the grooves in roll 65. The nonwoven web therefore is forced to conform to the shape of the grooves in roll 65 without either the bonding of the nonwoven web being affected, or the fibers in the nonwoven web being forced to yield. Skilled artisans are capable of adjusting the speed of web 63 and the dimensions and configurations of rollers (64, 65) to provide a creped nonwoven capable of bonding to apertured sheet 61.

Optionally, the process of FIG. 6 could include a creping knife located between the roll 65 and the screen 62. If a creping knife were used, then a separate lay on roll would be used to hold the unstabilized creped web against the screen.

The web leaving the roll 65 is in a creped conformation and impinges on the thermoplastic (molten) web 61 through pressure applied by roll 65 against-the nonwoven web and the molten web 61 and the perforated screen. The pressure, temperature and vacuum are sufficient together to cause a bond to be formed between the puckered nonwoven web leaving roll 65 and the perforated thermoplastic film that is formed when the molten web 61 cools below the melting point of the resin. A takeoff roll then removes the laminate of the puckered nonwoven web and the perforated film 66 from the screen 62.

Figure 7:
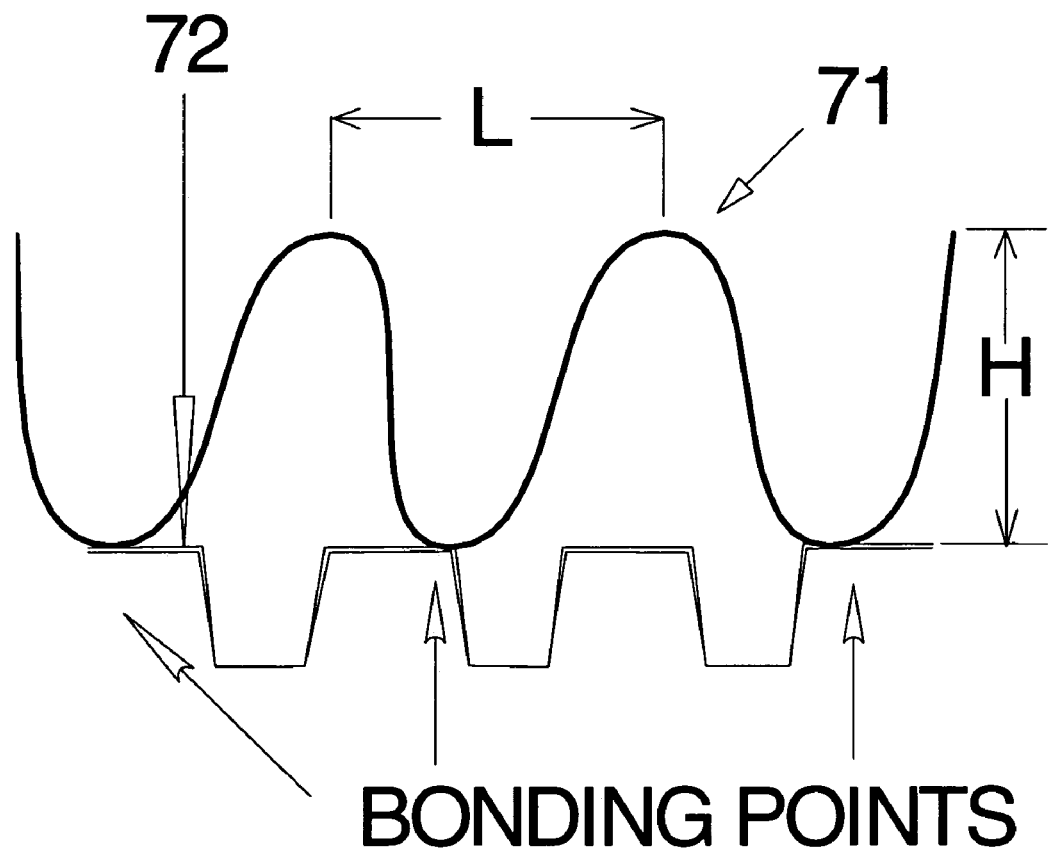
FIG. 7 is a cross sectional schematic view of a composite web of an embodiment the present invention.

FIG. 7 illustrates a preferred embodiment of the invention in which a creped web 71 is bonded to a three dimensional perforated film 72. The creped web is bonded to the perforated film at discrete points on the lands of the perforated film 72. These points are noted on the figure as "bonding points". The creped web is characterized by an average period L, and a height, H, where the ratio H/L provides an approximation to the extent to which the creped web is extensible by virtue of crepe induced extensibility. In a preferred embodiment of the invention, the value of H/L is greater than about 0.2, more preferably, greater than about 0.3, even more preferably, greater than about 0.4, and most preferably greater than about 0.5.

On the other hand, the magnitude of the crepe, which is determined by the H/L ratio, can be tailored to create bulkiness (e.g., high H/L), or mere flatness (e.g., low H/L), upon activation. Having a flat composite not only may be desirable in an adult incontinent product (i.e., the crepe does not show up on the outer wear), but is easy to package and convert at high conversion speeds. Accordingly, the ratio of H/L can vary anywhere from 0 to greater than about 2.5.

Figure 8:
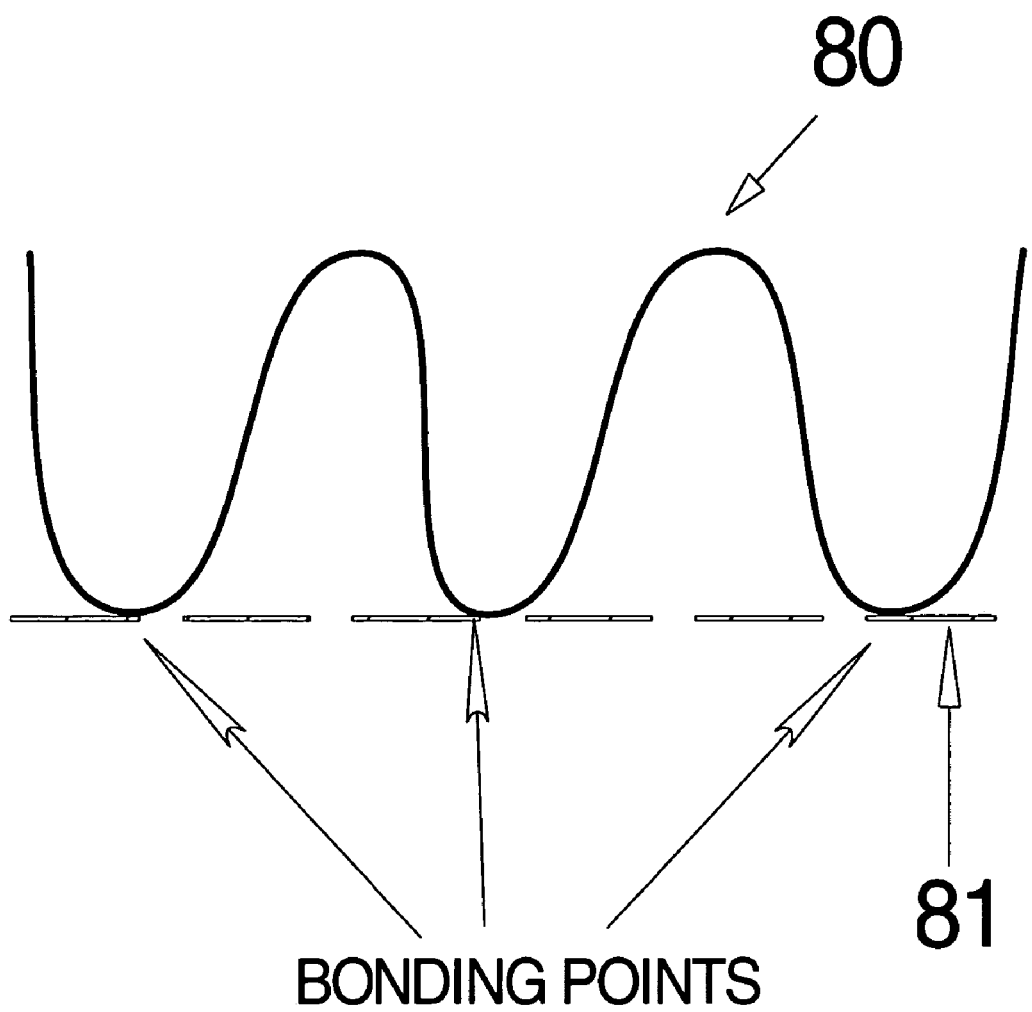
FIG. 8 is a cross sectional view of a further example of a composite web of an embodiment of the present invention.

FIG. 8 illustrates an alternative embodiment of the invention in which a creped web 80 is bonded to a two dimensional perforated film 81. As in the example of FIG. 7, there are discrete bonding points formed by the bonding process.

Figure 9:
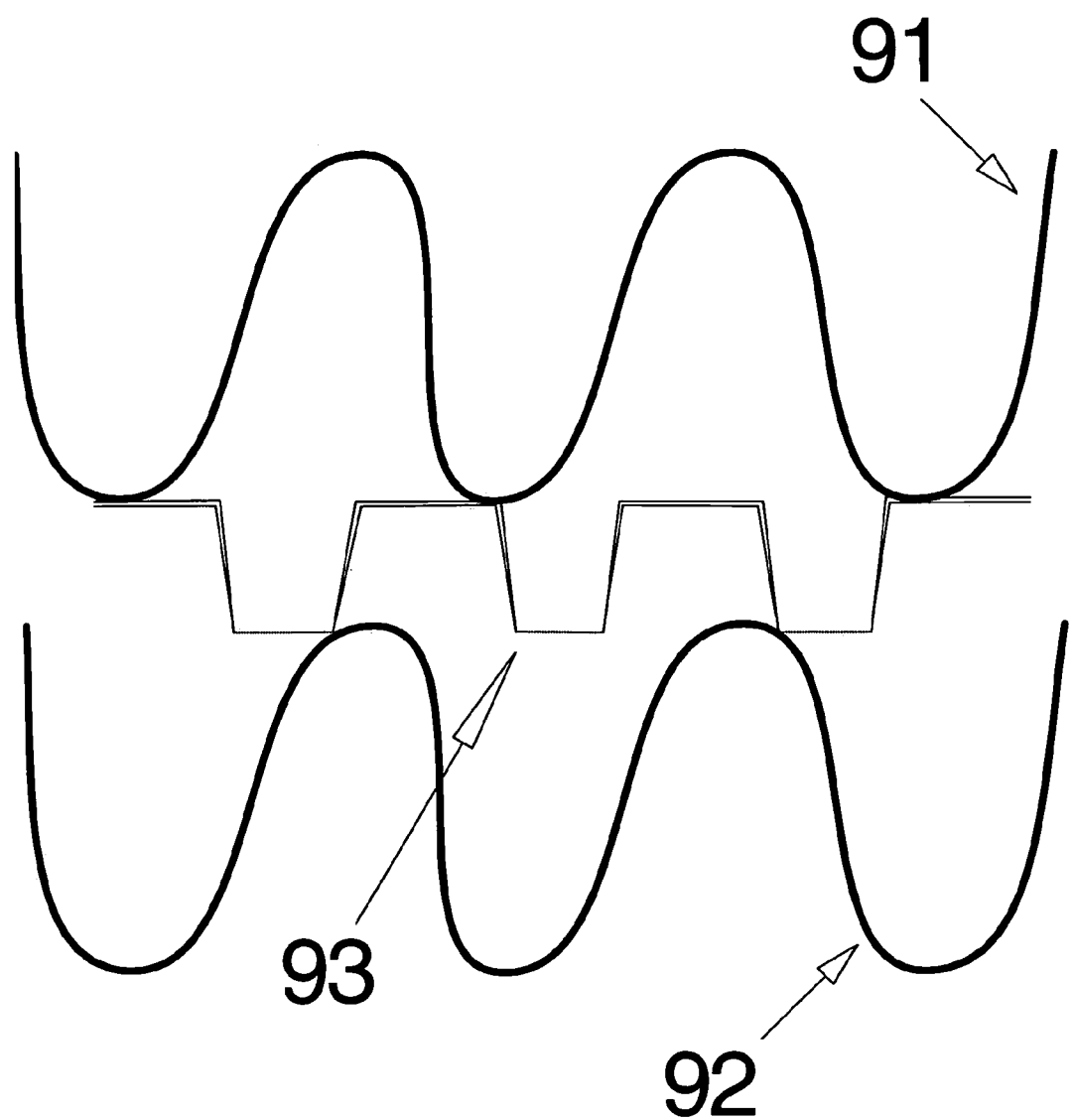
FIG. 9 is a cross sectional schematic view of an example of a three layer composite web of an embodiment of the present invention.

FIG. 9 illustrates a further embodiment of the invention in which two creped nonwoven layers (91 and 92) are bonded to a three dimensional perforated film 93. The web 91 is bonded to the continuous surface of the perforated film by discrete bonding points similar to those seen in FIG. 7. The bonding can be effected by vacuum lamination. The web 92 is bonded to points on the discontinuous surface of the perforated film, preferably by adhesive lamination, although any bonding mechanism can be used.

Figure 10:
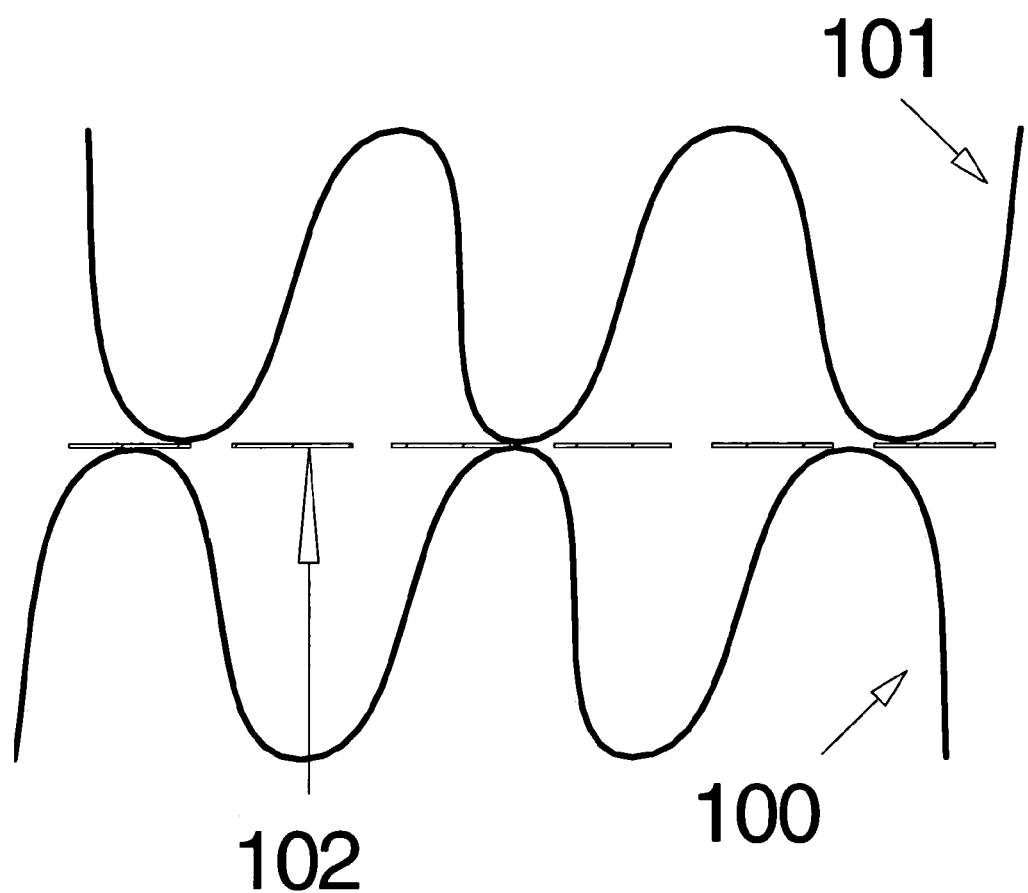
FIG. 10 is a cross sectional view of a second example of a three layer composite web of an embodiment of the present invention.

FIG. 10 illustrates yet a further embodiment of the invention in which two creped nonwoven webs (100 and 101) are bonded to a two dimensional perforated film 102. The perforated film 102 has two continuous surfaces and consequently, both webs can be bonded to the perforated web by any suitable bonding mechanism. In FIGS. 9 and 10, it should be noted that the webs on either side of the perforated elastic film are bonded to the film, and substantially not directly to each other, unless they fortuitously happen to meet at a hole in the film and are bonded therethrough.

The three dimensional elastic films of the invention typically are prepared by forming an elastic material under the impetus of vacuum or water (e.g, vacuum forming, or hydroforming). Such forming techniques are well known in the art, and any manner of forming a three dimensional apertured film now known or later discovered can be used in the invention. Two dimensional elastic films typically are prepared by stretching an elastic film to create small apertures or holes in the film, or by physically cutting the film. Those skilled in the art are capable of fabricating two or three dimensional elastic films using techniques well known in the art. Using the guidelines provided herein, skilled artisans Will be capable of creping an nonwoven web or other web, and then bonding the creped web to an elastic film (two or three-dimensional film) to provide an extensible composite web.

While the description of the present invention presented above has been limited to certain embodiments, it is recognized that similar advantages over the existing art can be obtained by other embodiments. Those skilled in the art will recognize that various changes and modifications can be made without departing from the spirit and scope of the present invention, and that all such modifications are within the scope of this invention.

We claim:

1. An absorbent article, comprising:
   a composite web comprising a creped nonwoven layer and a perforated elastic layer having first and second surfaces, the perforated elastic layer and said creped nonwoven layer being bonded together at bonding points consisting essentially of a plurality of points on said first surface and a plurality of points on the nonwoven layer, wherein the elastic layer comprises a first non-elastic skin layer; a second non-elastic skin layer; and an elastic core between the first and second skin layers.

2. The absorbent article of claim 1 wherein the elastic layer comprises a three-dimensional apertured film.

3. The absorbent article of claim 1 wherein the elastic layer comprises a two-dimensional apertured film.

4. A composite web comprising a creped nonwoven layer and a perforated elastic layer having first and second surfaces, the perforated elastic layer and said creped nonwoven layer being bonded together at bonding points consisting essentially of a plurality of points on said first surface and a plurality of points on the nonwoven layer, wherein said nonwoven layer is constructed of a non-elastic material and said nonwoven layer is activated.

5. The absorbent article of claim 4 wherein the elastic layer comprises a three-dimensional apertured film.

6. The absorbent article of claim 4 wherein the elastic layer comprises a two-dimensional apertured film.

* * * * *